United States Patent [19]

Simonin

[11] Patent Number: 4,522,210
[45] Date of Patent: Jun. 11, 1985

[54] METHOD OF SKIN TREATMENT AND DEVICE FOR CARRYING OUT THE SAID METHOD

[76] Inventor: Philippe Simonin, 30 Allée Horace, Vernet 78170 La Celle St. Cloud, France

[21] Appl. No.: 478,025

[22] Filed: Mar. 23, 1983

[30] Foreign Application Priority Data

Apr. 2, 1982 [FR] France .................. 82 05796

[51] Int. Cl.³ .......................... A61N 1/00
[52] U.S. Cl. ............................. 128/421
[58] Field of Search ............ 128/303.13, 303.17, 128/303.18, 419 R, 421, 907

[56] References Cited

U.S. PATENT DOCUMENTS

| | | | |
|---|---|---|---|
| 3,064,641 | 11/1962 | Manenti et al. | 128/419 R |
| 3,897,789 | 8/1975 | Blanchard | 128/303.18 |
| 3,946,745 | 3/1976 | Hsiang-Lai et al. | 128/421 |
| 4,155,363 | 5/1979 | Letchworth et al. | 128/303.18 |
| 4,372,315 | 2/1983 | Shapiro et al. | 128/303.18 |

FOREIGN PATENT DOCUMENTS 701240 12/1967 Belgium .
839556 6/1939 France .
2430225 2/1980 France .

*Primary Examiner*—William E. Kamm
*Assistant Examiner*—Mitchell J. Shein
*Attorney, Agent, or Firm*—Steinberg & Raskin

[57] ABSTRACT

This invention essentially relates to a method of using a pulse generator for aesthetic treatment of the skin with a view to removing wrinkles, puckers or the like therefrom, which consists in connecting to the said pulse generator a needle which is introduced immediately under the skin and in substantially parallel relationship to the wrinkle or pucker to be removed, and in making pass through the said needle a weak current of preferably low frequency comprised between about 100 and 500 cps to thus fill up the depression of the pucker or the wrinkle.

4 Claims, 1 Drawing Figure

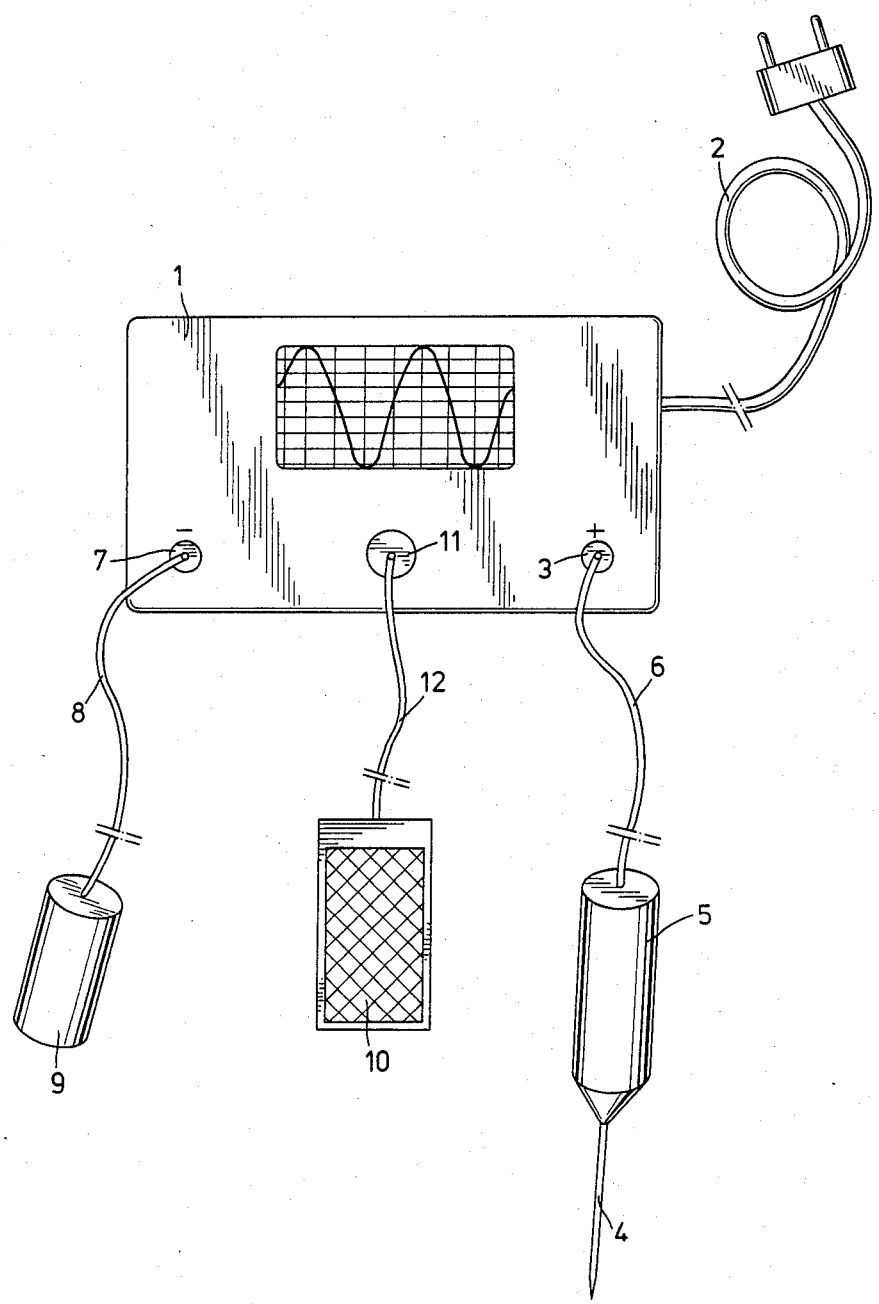

METHOD OF SKIN TREATMENT AND DEVICE FOR CARRYING OUT THE SAID METHOD

The present invention has essentially for a subject matter a method of skin treatment.

It is also directed to a device for carrying out the said method.

There are already known various methods and means for treating or rejuvenating the skin, which allow smoothing out at least temporarily the wrinkles, puckers or the like appearing naturally on the human body, particularly on the face, in course of aging of the skin.

Thus, it is already known to rejuvenate the skin of the face by way, particularly, of external or topical application of certain cosmetic products prepared in the form of, for example, creams or ointments. It is also known to smooth out the wrinkles or various irregularities appearing on the epidermis by mechanical means, that is, for example, by grinding or by using various abrasive means.

But all such skin treating means for external use suffer from a certain number of disadvantages. Although they allow levelling off and therefore rejuvenating the skin to a certain extent, they remain, however, very expensive, for they require the use of special materials or products. Moreover, they do not allow accurate and localized treatment of the wrinkle or of the region to be treated and are apt to cause burns or various damages which risk spoiling the skin both in the regions requiring treatment and those needing no such treatment.

It is also known to treat wrinkles by injecting placenta or silicone extracts into the derm. Such injections of course allow refilling the wrinkles or the puckers at the surface of the epidermis, but they also have disadvantages because of the necessarily high cost of the products to be injected and also, of course, because of the risk of bleeding involved.

The present invention has as a purpose to remedy all the above drawbacks, as well as other drawbacks, by providing a novel method and a novel device which do not require the use of any special product, are inexpensive and offer all the desired qualities of efficiency resulting in considerable attenuation of the wrinkles and improvement of the skin of the treated subject.

To this end, the invention has for a subject matter a method of using a pulse generator for aesthetic treatment of the skin with a view to removing therefrom wrinkles, puckers or the like, characterized in that it consists in connecting to the said pulse generator a needle which is introduced immediately under the skin and in substantially parallel relationship to the wrinkle or the pucker to be removed, and in making pass through the said needle a weak current at a preferably low frequency comprised between about 100 and 500 cps to thus fill up the depression or hollow formed by the pucker or the wrinkle.

It is thus understood that, in contrast to the prior methods which consisted of either an external treatment or of a deep injection into the derm of a special product, the method of the invention consists in effecting a mere "skin-deep" prick involving no risk of bleeding or of spoilage of the skin in any manner whatsoever, since said prick is effected in almost tangential relationship to the skin outer surface. Such a prick has a local and very accurate effect upon the wrinkle to be treated, due to the fact that the weak current of appropriate frequency flowing through the needle has a highly localized reactivating effect upon the tissues resulting in durably filling up the void or the depression formed by the wrinkle.

It has indeed been noticed by Applicant that it is essentially within the range of low frequencies that surprising and durable results are obtained in levelling up and beautifying the skin.

According to another feature of the inventive method, the needle is connected to the positive terminal of the said generator.

It should be added here that the method of the invention is also characterized in that the said current is made to flow through the needle at intervals comprised between about one and a few seconds depending on the nature of the region to be treated.

It should also be noted that in view of the extremely small depth of the prick and the very weak current flowing through the needle, no particular pain is felt by the person under treatment.

The invention is also directed to a device for carrying out the method complying with the above-mentioned characteristics, and of the type comprising a pulse generator, e.g. of low frequency, the said device being essentially characterized by a thin needle connected to the positive terminal of the said generator and by a current return electrode connected to the negative terminal of the generator.

The said device is also characterized in that the said generator is equipped with a pedal for interrupting at will the flow of current through the needle.

According to still another characterizing feature of the device, the generator comprises a mains frequency rectifier circuit.

Furthermore, the frequency and strength of the generator output current may be variable.

Other characterizing features and advantages of the invention will appear more clearly as the following detailed description proceeds with reference to the appended drawing, the single FIGURE of which is a diagrammatic view of the apparatus designed according to the principle of the invention.

According to one example of embodiment, and referring to the appended single FIGURE, it is seen that a device according to the invention comprises essentially a pulse generator 1 connected to the mains through conductor means 2 and to the positive terminal 3 of which is connected a very thin needle 4. More precisely, the needle 4 is connected to the positive terminal 3 of generator 1 through a flexible lead 6 and is mounted removably, by any appropriate means, at the end of a handle or grip element 5 intended to be grasped by the user.

To the negative terminal 7 of generator 1 is connected through the medium of a cable 8 a current return electrode 9, e.g. merely cylindrical in shape and intended to be held in the hand of the person under treatment.

There is diagrammatically shown at 10 a pedal connected at 11 to the generator 1 through the medium of conductor means 12. The pedal 10, which may be operated by the foot, constitutes a switch means allowing the current to be passed at will through the needle 4 at time intervals comprised for example between about one and a few seconds depending on the nature of the tissue to be treated, as will be explained in detail later.

The means forming the generator 1 do not need to be described in detail here. It will only be mentioned that it comprises preferably a mains frequency rectifier circuit, in such a manner that a current of very low strength and of low frequency comprised between about 100 and 500 cps can be made to pass through the needle 4, thus imparting to the treatment maximum efficiency. The generator 1 may of course, without departing from the scope of the invention, comprise all the necessary elements for varying the frequency and strength of the current at the output 3 of the generator depending on the tissues which are to be treated and the results to be obtained. For example, a 100-cps frequency may be used to treat some particular location of the face, whereas another, predetermined frequency higher than 100 cps, e.g. 400 cps, can be employed to treat some other part of the face. This means that the invention encompasses any generator apt to produce a current of low strength and of a frequency even exceeding the aforementioned frequency range.

There will now be described the operation and use of the above apparatus.

The generator 1 having been switched on and the person to be treated holding in his hand the electrode 9, the operator takes hold of the needle 4 by its support 5 and introduces the needle right under the skin, i.e., immediately under the wrinkle to be treated. This causes no pain nor bleeding, owing to the extremely small depth of penetration of the needle. It is essential that the prick should be performed in substantially parallel relationship to the surface of the epidermis, i.e. substantially parallel to the wrinkle to be treated. Once the prick is made, the operator acts upon the pedal 10 to cause a weak current, of a frequency of for example 100 cps, to flow through the needle 4, it being understood, once again, that the generator 1 may be designed to allow varying the frequency and setting it at a higher value depending on the nature of the wrinkle to be treated and on the results sought. Likewise, by means of the pedal 10, the number of pulses and the current flow duration may be caused to vary depending on the nature of the wrinkles to be treated.

As a result, the flow of current will bring about in the tissues a reactivation of the cellular metabolism or induce a small inflammatory reaction producing an exudate capable of filling up the void or the depression or hollow formed by the wrinkle, which will thus be levelled up. Of course, the operation may be repeated if, after some time, the wrinkle should again fall in or should reappear, but, in the long run, the wrinkle is very considerably and durably attenuated owing to the improved vitality of the tissues obtaining under the wrinkle after several excitations resulting from the current of low strength and low frequency flowing through the needle.

For example, Applicant has found that a frequency of 400 cps ensures a durable attenuation of from 50 to 80% of the wrinkles in the region of the lips after a course of five treatments. Also, by using a frequency of 100 cps for wrinkles in the region of the eyes or the rings round them, a durable attenuation of from 30 to 50% of the said wrinkles is obtained, at the rate of about 5% per treatment, and this in a cumulative manner.

Of course the thin needle 4 may be variously shaped and dimensioned in cross-section depending on the tissues to be treated, the only requirement being that the needle remain relatively thin to allow it to penetrate into the skin very close to its surface without risking spoiling it or producing clefts, cracks or tears, which must be avoided at any cost, as can be easily understood. Likewise, the means for removably securing the needle 4 on the element 5, as well as the various components of the generator 1, can be selected in any suitable manner without departing from the scope of the invention.

There is therefore obtained, according to the invention, a method and an apparatus for treating wrinkles by means of a weak current of low frequency "injected" by pricking the skin right under, and in parallel relationship to, the wrinkles or puckers to be treated, and allowing the skin to be improved or beautified lastingly, without any risk of deteriorating it and without any pain to the person undergoing the treatment.

It will be noted that since wrinkles are not a disease but rather a normal and natural phenomenon which occurs in course of ageing of the skin, the method of the invention should in no case be considered a therapeutic or curative method. Also, it should be stressed here that the needle introduced immediately under the surface of the skin, in parallel relationship to the wrinkle, causes no bleeding and does not serve to introduce any product into the skin, which would be typical of a medical act. Besides, the method of the invention can perfectly and lawfully be carried out by a person who is not a doctor, such as for example a beautician or like aesthetician.

Of course, the skin treating method and device according to the invention must not be considered as applying limitatively to the treatment of wrinkles. Indeed, they may apply generally to the treatment of any irregularities of the skin, such as for example scars, wheals, without however departing from the scope of the invention.

What is claimed is:

1. Method for the aesthetic treatment of wrinkled or puckered skin having depressions from the wrinkle or pucker to remove such wrinkles and puckers from the skin, which comprises introducing a needle immediately under the skin and in substantially parallel relationship to the wrinkle or pucker to be removed, said needle being connected to a positive terminal of a low frequency generator having a current return electrode connected to the negative terminal thereof, and passing a low frequency current of between about 100 and 500 cps through said needle for a time sufficient to effect filling of the depression of the wrinkle or pucker, thus improving the aesthetic appearance of the skin.

2. Method according to claim 1 wherein the time of the treatment is between about 1 and several seconds.

3. Method according to claim 1 wherein the frequency is about 400 cps.

4. Method according to claim 1 wherein a frequency of about 100 cps is used in treatment of wrinkles in the region of the eyes.

* * * * *